United States Patent
Koch et al.

(10) Patent No.: US 10,772,142 B2
(45) Date of Patent: Sep. 8, 2020

(54) WIRELESS CONNECTION TO PERIPHERAL DEVICE BASED ON ADVERTISEMENT CADENCE

(71) Applicant: Medtronic, Inc., Minneapolis, MN (US)

(72) Inventors: Christopher D. Koch, Minneapolis, MN (US); Corey G. Thompson, Apple Valley, MN (US); Yibiao Lu, Eden Prairie, MN (US); Gautham Ravindran, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 111 days.

(21) Appl. No.: 16/044,758

(22) Filed: Jul. 25, 2018

(65) Prior Publication Data

US 2020/0037378 A1    Jan. 30, 2020

(51) Int. Cl.
*H04W 12/00* (2009.01)
*H04W 76/14* (2018.01)
(Continued)

(52) U.S. Cl.
CPC ........... *H04W 76/14* (2018.02); *H04W 8/005* (2013.01); *H04W 76/11* (2018.02)

(58) Field of Classification Search
None
See application file for complete search history.

(56) References Cited

U.S. PATENT DOCUMENTS 8,971,807 B2   3/2015   Hillyard
9,572,992 B2   2/2017   Shahandeh et al.
(Continued)

FOREIGN PATENT DOCUMENTS

EP   2878334 A1   6/2015
JP   2017126951   7/2017
(Continued)

OTHER PUBLICATIONS

International Search Report and Written Opinion of International Application No. PCT/US2019/042557, dated Oct. 2, 2019, 12 pp.
Bluetooth protocol in Apple iOS is provided in About Core Bluetooth, Apple Inc., available at https://developer.apple.com/library/content/documentation/NetworkingInternetWeb/Conceptual/CoreBluetooth_concepts/AboutCoreBluetooth/Introduction.html (retrieved Apr. 23, 2018), 3 pp.

(Continued)

*Primary Examiner* — Noel R Beharry
*Assistant Examiner* — Lionel Preval

(57) ABSTRACT

Techniques, systems, devices, and methods are disclosed for establishing a communication session with a peripheral device. In one example, a device includes a memory and processing circuitry configured to store and execute an operating system (OS) and an application for execution on the OS. The application receives an object handle for establishing a wireless connection to a peripheral device. The application determines, based on the object handle, an advertisement cadence for the peripheral device that comprises periods of time wherein the peripheral device is discoverable interleaved with periods of time wherein the peripheral device is non-discoverable. At a time determined based on the advertisement cadence, the application issues, using the object handle, a request that the OS establish the wireless connection to the peripheral device, such that the OS establishes the wireless connection to the peripheral device during one of the periods of time wherein the peripheral device is discoverable.

35 Claims, 6 Drawing Sheets

(51) Int. Cl.
*H04W 76/11* (2018.01)
*H04W 8/00* (2009.01)

(56) References Cited

U.S. PATENT DOCUMENTS

| | | | |
|---|---|---|---|
| 9,687,658 | B2 | 6/2017 | Wu et al. |
| 9,855,433 | B2 | 1/2018 | Shahandeh et al. |
| 9,894,691 | B1 | 2/2018 | Hellman et al. |
| 2012/0003933 | A1* | 1/2012 | Baker .................. H04W 4/029 455/41.2 |
| 2015/0201455 | A1 | 7/2015 | Redding et al. |
| 2016/0287887 | A1 | 10/2016 | Wu et al. |
| 2017/0157411 | A1 | 6/2017 | Shahandeh et al. |
| 2017/0216611 | A1 | 8/2017 | Yoder et al. |
| 2017/0312530 | A1 | 11/2017 | Schilling et al. |
| 2018/0021589 | A1 | 1/2018 | Wu et al. |
| 2018/0028827 | A1 | 2/2018 | Schilling et al. |
| 2018/0049251 | A1 | 2/2018 | Hellman et al. |
| 2018/0063784 | A1* | 3/2018 | Abraham .......... H04W 52/0216 |
| 2018/0078777 | A1* | 3/2018 | Wu .................... A61N 1/37252 |
| 2018/0152972 | A1 | 5/2018 | Wu et al. |
| 2019/0029060 | A1 | 1/2019 | Kyou |

FOREIGN PATENT DOCUMENTS

| | | |
|---|---|---|
| JP | 2017126951 A | 7/2017 |
| WO | 2017122429 A1 | 7/2017 |

OTHER PUBLICATIONS

Bluetooth LE protocol in Apple iOS is provided in Core Bluetooth, Apple Developer Documentation, Apple Inc., available at https://developer.apple.com/documentation/corebluetooth (retrieved Apr. 23, 2018), 4 pp.

"Bluetooth low energy overview," available at https://developer.android.com/guide/topics/connectivity/bluetooth-le (retrieved Jul. 25, 2018), 12 pp.

"Bluetooth overview," available at https://developer.android.com/guide/topics/connectivity/bluetooth (retrieved Jul. 25, 2018), 20 pp.

(PCT/US2019/042557) PCT Notification of Transmittal of the International Search Report and the Written Opinion of the International Searching Authority, dated Oct. 2, 2019, 12 pages.

Response to Written Opinion dated Oct. 2, 2019, from International Application No. PCT/US2019/042557, dated Jan. 10, 2020, 16 pp.

International Preliminary Report on Patentability from International Application No. PCT/US2019/042557, dated Feb. 25, 2020, 6 pp.

* cited by examiner

WIRELESS CONNECTION TO PERIPHERAL DEVICE BASED ON ADVERTISEMENT CADENCE

TECHNICAL FIELD

This disclosure relates generally to wireless connectivity between a central device and a peripheral device, and more specifically, to establishing a wireless communication session between an external computing device and an implantable medical device.

BACKGROUND

Implantable medical devices (IMDs) may be surgically implanted in a patient to monitor one or more physiological parameters of the patient and/or deliver therapy to suppress one or more symptoms of the patient. For example, an IMD may comprise a cardiac monitor, be configured to deliver cardiac pacing or another stimulation therapy to the patient, and/or be configured to terminate tachyarrhythmia by delivery of high energy shocks. A clinician or patient may use an external computing device to retrieve information collected by the IMD and/or to configure or adjust one or more parameters of the therapy provided by the IMD. Typically, the external computing device connects to the IMD via a wireless connection. In some examples, a wireless connection is established between the external computing device and the IMD using the Bluetooth® wireless protocol. In such an example, the external computing device is treated as a central device, and one or more IMDs are treated as peripheral devices.

SUMMARY

In general, the disclosure describes techniques for establishing a wireless communication session between an external computing device, such as a smartphone or other mobile computing device, and a peripheral device, such as an IMD. Some types of IMDs, such as IMDs that provide cardiac pacing therapy, have single-use batteries that last for multiple years. Maximizing battery life of an IMD is an extremely important design factor, particularly for those with single-use batteries because a patient must undergo surgery to remove and replace the IMD upon depletion of the battery.

Because the IMD is implanted within the patient, a clinician or a patient uses an external computing device to configure or control the monitoring and/or therapy provided by the IMD over a wireless connection. In some examples, the external computing device and IMD may be modeled as a master and slave device, respectively, or as a "central" and a "peripheral" device, respectively. Wireless radios in IMDs may be relatively power-intensive. Inefficient use or overuse of the wireless radio may drain the battery power of the IMD, thereby shortening the lifetime of the IMD and increasing the number of IMD maintenance surgeries necessary for the patient to undergo.

In some examples, an IMD implements an advertisement cadence to reduce the power consumption of the wireless radio. The advertisement cadence comprises periods of time wherein the IMD is discoverable interleaved with periods of time wherein the IMD is non-discoverable. During the periods of time when the IMD is discoverable, the IMD activates its wireless radio and issues advertisements indicating the availability of the IMD for a wireless connection. During the periods of time when the IMD is not discoverable, the IMD deactivates its wireless radio to conserve power. The external computing device scans for advertisements indicating the presence or availability of one or more IMDs. In response to detecting an advertisement, the external computing device may elect to establish a connection to the IMD. However, during the time the external computing device requires to process and complete the wireless connection, the period of time when the IMD is discoverable may expire, causing the IMD to deactivate the wireless radio of the IMD and abort the connection attempt. Conventionally, the external computing device may attempt to reconnect to the IMD by trial-and-error numerous times, which may result in multiple failed connection attempts. These failed connection attempts, over the lifetime of the IMD, result in increased power usage of the wireless radio of the IMD, and therefore reduce the battery lifetime of the IMB. For an IMB which may be implanted in a patient for extended periods of time, this cumulative increased power usage may reduce the battery lifetime of the IMD by several months or even years.

Techniques are disclosed herein for establishing a wireless communication session between an external computing device and an IMD which may reduce the number of failed connection attempts, thereby increasing the battery lifetime of the IMD. In one example, an external computing device receives an advertisement from an IMD indicating an availability of the IMD for a connection. Based on the advertisement, the external computing device determines an advertisement cadence for the IMD. The external computing device issues a request to establish the wireless connection to the IMD at a time determined based on the advertisement cadence, such that the wireless connection to the IMD is established during one of the periods of time wherein the IMD is discoverable. Thus, such techniques as disclosed herein may increase the likelihood that a connection attempt succeeds, thereby reducing the power usage of the IMD when establishing wireless connections. By reducing the power usage of the IMD using the techniques disclosed herein, an IMD may have increased battery lifetime, thereby reducing the number of IMD maintenance surgeries necessary for the patient to undergo. Furthermore, such techniques as disclosed herein may reduce the length of time required between the discovery of an IMD by an external device and the successful establishment of a wireless connection between the IMD and external device. Such techniques may be particularly useful where an IMD must convey time-sensitive or critical information to the external device.

In one example, this disclosure describes a method comprising: receiving, by an application executing on an operating system executing on processing circuitry of an external computing device, an object handle for establishing a wireless connection to a peripheral device; determining, by the application and based on the object handle, an advertisement cadence for the peripheral device, wherein the advertisement cadence comprises periods of time wherein the peripheral device is discoverable interleaved with periods of time wherein the peripheral device is non-discoverable; and at a time determined based on the advertisement cadence, issuing, by the application and using the object handle, a request that the operating system establish the wireless connection to the peripheral device, such that the operating system establishes the wireless connection to the peripheral device during one of the periods of time wherein the peripheral device is discoverable.

In another example, this disclosure describes a device comprising: a memory configured to store an operating system and an application for execution on the operating system; and processing circuitry configured to execute the operating system and the application, wherein the application is configured to: receive an object handle for establishing a wireless connection to a peripheral device; determine, based on the object handle, an advertisement cadence for the peripheral device, wherein the advertisement cadence comprises periods of time wherein the peripheral device is discoverable interleaved with periods of time wherein the peripheral device is non-discoverable; and at a time determined based on the advertisement cadence, issue, using the object handle, a request that the operating system establish the wireless connection to the peripheral device, such that the operating system establishes the wireless connection to the peripheral device during one of the periods of time wherein the peripheral device is discoverable.

In another example, this disclosure describes a system comprising: a peripheral device comprising communication circuitry, wherein the peripheral device further comprises an advertisement cadence, and wherein the advertisement cadence comprises periods of time wherein the peripheral device is discoverable interleaved with periods of time wherein the peripheral device is non-discoverable; and an external computing device comprising: a memory configured to store an operating system and an application for execution on the operating system; and processing circuitry configured to execute the operating system and the application, such that the application is configured to: receive an object handle for establishing a wireless connection to a peripheral device; determine, based on the object handle, the advertisement cadence for the peripheral device; and at a time determined based on the advertisement cadence, issue, using the object handle, a request that the operating system establish the wireless connection to the peripheral device, such that the operating system establishes the wireless connection to the peripheral device during one of the periods of time wherein the peripheral device is discoverable.

In another example, this disclosure describes a non-transitory, computer-readable medium comprising instructions that, when executed, cause processing circuitry of an external computing device to execute an operating system and an application, such that the application is configured to: receive an object handle for establishing a wireless connection to a peripheral device; determine, based on the object handle, an advertisement cadence for the peripheral device, wherein the advertisement cadence comprises periods of time wherein the peripheral device is discoverable interleaved with periods of time wherein the peripheral device is non-discoverable; and at a time determined based on the advertisement cadence, issue, using the object handle, a request that the operating system establish the wireless connection to the peripheral device, such that the operating system establishes the wireless connection to the peripheral device during one of the periods of time wherein the peripheral device is discoverable.

This summary is intended to provide an overview of the subject matter described in this disclosure. It is not intended to provide an exclusive or exhaustive explanation of the apparatus and methods described in detail within the accompanying drawings and description below. Further details of one or more examples are set forth in the accompanying drawings and the description below.

BRIEF DESCRIPTION OF DRAWINGS

Like reference characters refer to like elements throughout the figures and description.

DETAILED DESCRIPTION

Figure 1:
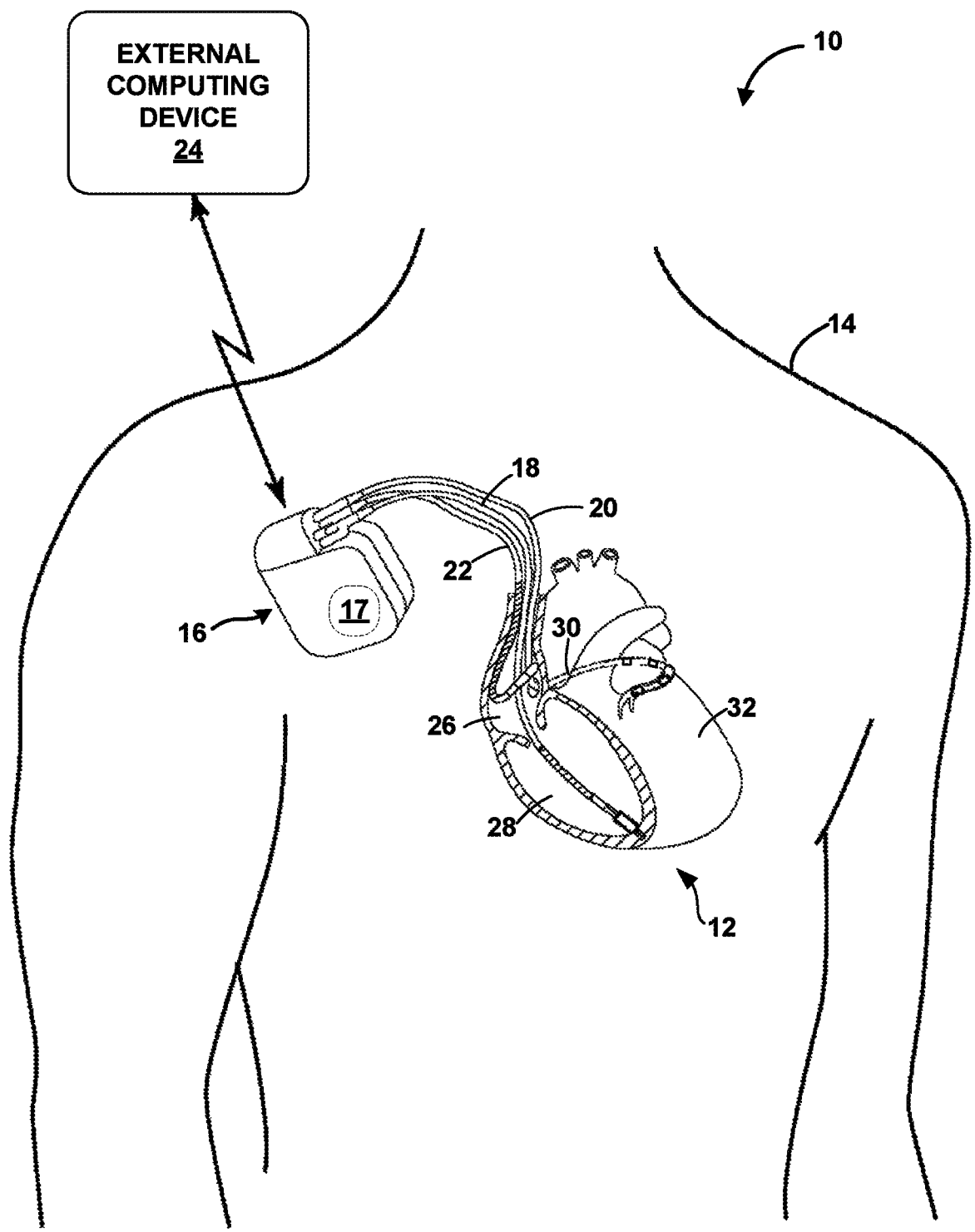
FIG. 1 is a block diagram illustrating a system for establishing a communication session with an IMD in accordance with the techniques of the disclosure.

In some examples, an IMD implements an advertisement cadence to reduce the power consumption of the wireless radio. The advertisement cadence comprises periods of time wherein the IMD is discoverable interleaved with periods of time wherein the IMD is non-discoverable. As used herein, an IMD is "discoverable" when the IMD activates its wireless radio and issues advertisements indicating the availability of the IMD for a wireless connection. The IMD is discoverable in that the IMD advertises its availability for establishing a connection (e.g., by transmitting an advertisement indicating such availability to a central device) such that the central device may "discover" the presence of the IMD and establish a wireless connection with the IMD. In contrast, the IMD is not discoverable during a period of time in which the IMD deactivates its wireless radio to conserve power (e.g., such that the central device may be unable to "discover" the IMD because the IMD is not capable of transmitting or receiving wireless communications.

Conventionally, to establish a wireless connection between an external computing device and an IMD, the following operations occur. An external computing device may scan for available devices. During such a scan, and during a period of time that the IMD is discoverable, the IMD activates its wireless radio and issues advertisements indicating the availability of the IMD for a wireless connection. In response to detecting an advertisement, the external computing device issues a scan request to the IMD to request additional data. In response to receiving the scan request, the IMD issues a scan response to the external device that includes the additional data. In response to receiving the scan request, an operating system for the external device processes the wireless connection and transmits a connection request to the IMD. If the IMD receives the connection request while the IMD is still discoverable, the IMD will complete the connection.

However, during the time an external computing device requires to process and complete a wireless connection with an IMD by issuing a connection request, the period of time when the IMD is discoverable may expire, causing the IMD to deactivate the wireless radio of the IMD and abort the connection attempt. For example, the external computing device and the IMD may have separate, asynchronous clock domains, and the external computing device's duty cycle for scanning is independent from the IMD's duty cycle for advertising. As another example, the external computing device may require a length of time to initiate and establish the wireless connection that is longer than a length of time that the IMD remains discoverable. For example, an application executing on the external computing device may communicate, to an operating system of the external computing device, a request to connect to the IMD, and the delay imposed by the operating system in responding to the request and establishing the connection may be longer than the length of time that the IMD remains discoverable.

Conventionally, if the external computing device cannot process a connection indication to an IMD before the IMD stops accepting connections, the two devices will be unable to create a connection. In response to a failure of the connection attempt, the external computing device may attempt to re-connect to the IMD by trial-and-error numerous times, which may result in multiple failed connection attempts. Further, in the operation described above, each failed connection attempt requires the IMD to transmit, for example, at least one scan response, which uses the wireless radio and consumes power. These failed connection attempts, over the lifetime of the IMD, result in increased power usage of the wireless radio of the IMD, and therefore reduce the battery lifetime of the IMD, and therefore reduce the battery lifetime of the IMD. For an IMD which may be implanted in a patient for extended periods of time, this cumulative increased power usage may reduce the battery lifetime of the IMD by several months or even years. Furthermore, when an IMD is discoverable (e.g., when the IMD advertises that it is available for a connection), the IMD may have time-critical information that must be reliably and quickly conveyed to the external computing device. Conversely, the external computing device may increase its scanning duty cycle, thereby increasing its power usage, when the external computing device is attempting to convey a higher-order function to higher-order functions of the IMD. By increasing the scanning duty cycle, the external computing device may increase the likelihood that the external computing device may detect an advertisement of the IMD and establish a connection. However, using a higher scanning duty cycle increases the power consumption of the external computing device. In examples where the external computing device is a mobile device, increasing the power consumption may negatively affect battery life of the mobile device, which may adversely affect the user.

Another possible solution to this problem is to extend the advertisement interval of the IMD. For example, the time for an IMD to accept a connection request may be extended to a period of time longer than the implementation time required by the external computing device to process a connection request. However, based on the desired number of connections expected over a defined period, the energy used to extend the advertisement interval of the IMD may result in substantially reduced battery life of the IMD.

Yet another possible solution is to repeatedly and continuously attempt to connect to the IMD by issuing connection requests. For example, each time an operating system of the external computing device times out a connection request from an application executing on the external computing device because the IMD is not advertising, the application may reissue a connection request, and repeat the cycle of connection request and timeout until the IMD resumes advertising and the connection establishes. However, if the cadence of the IMD advertising is longer than the connection timeout period of the external computing device, then there may be several cycles of timeouts, which may cause the external computing device to be in an energy-intensive loop. In examples, where the external computing device is a smartphone of a patient, excessive power consumption by the external computing device may be inconvenient or unacceptable to the patient. Further, if a period of time required for the timeout and subsequent reissue of the connection request occurs on a period with the IMD advertisement cadence, and/or takes longer than the IMD advertisement cadence, the connection request still may not be issued during a period of time when the IMD is discoverable such that the IMD may receive the request.

Accordingly, techniques are disclosed herein for establishing a wireless communication session between an external computing device and an IMD which may reduce the number of failed connection attempts, thereby increasing the battery lifetime of the IMD and, in some cases, the external computing device. In some examples, the wireless communication session is a Bluetooth® or a Bluetooth® Low Energy (BLE) wireless communication session. In one example, an external computing device receives an advertisement from an IMD indicating an availability of the IMD for a connection. Based on the advertisement, the external computing device determines an advertisement cadence for the IMD. The external computing device issues a request to establish the wireless connection to the IMD at a time determined based on the advertisement cadence, such that the wireless connection to the IMD is established during one of the periods of time wherein the IMD is discoverable. Thus, such techniques as disclosed herein may increase the likelihood that a connection attempt succeeds and/or the reliability of establishing the wireless connection, thereby reducing the power usage of the IMD when establishing wireless connections. By reducing the power usage of the IMD using the techniques disclosed herein, an IMD may have increased battery lifetime, thereby reducing the number of IMD maintenance surgeries necessary for the patient to undergo. Furthermore, such techniques as disclosed herein may reduce the length of time required between the discovery of an IMD by an external device and the successful establishment of a wireless connection between the IMD and external device. Such techniques may be particularly useful where an IMD must convey time-sensitive or critical information to the external device.

FIG. 1 is a block diagram illustrating system 10 for establishing a communication session with IMD 16 in accordance with the techniques of the disclosure. As illustrated by example system 10 in FIG. 1, IMD 16 may, in some examples, be an implantable cardiac pacemaker, implantable cardioverter/defibrillator (ICD), or pacemaker/cardioverter/defibrillator, for example. IMD 16 is connected to leads 18, 20 and 22 and is communicatively coupled to external computing device 24. IMD 16 senses electrical signals attendant to the depolarization and repolarization of heart 12, e.g., a cardiac electrogram (EGM), via electrodes on one or more leads 18, 20 and 22 or the housing of IMD 16. IMD 16 may also deliver therapy in the form of electrical signals to heart 12 via electrodes located on one or more leads 18, 20 and 22 or a housing of IMD 16. The therapy may be pacing, cardioversion and/or defibrillation pulses. IMD 16 may monitor EGM signals collected by electrodes on leads 18, 20 or 22, and based on the EGM signal, diagnose, and treat cardiac episodes.

In some examples, IMD 16 includes communication circuitry 17 including any suitable circuitry, firmware, software, or any combination thereof for communicating with another device, such as external device 24 of FIG. 1. For example, communication circuitry 17 may include one or more processors, memory, wireless radios, antennae, transmitters, receivers, modulation and demodulation circuitry, filters, amplifiers, or the like for radio frequency communication with other devices, such as external device 24. IMD 16 may use such communication circuitry to, for example, transmit one or more advertisements indicating the availability of the IMD for a wireless connection during a period of time wherein IMD 16 is discoverable. Further, IMD 16 may deactivate communication circuitry 17 to conserve power during a period where IMD 16 is non-discoverable. Upon establishing a wireless connection to external device 24 as described below, IMD 16 may use communication circuitry 17 to receive downlinked data from to control one or more operations of IMD 16 and/or send uplinked data to external device 24.

Leads 18, 20, 22 extend into the heart 12 of patient 14 to sense electrical activity of heart 12 and/or deliver electrical stimulation to heart 12. In the example shown in FIG. 1, right ventricular (RV) lead 18 extends through one or more veins (not shown), the superior vena cava (not shown), and right atrium 26, and into right ventricle 28. Left ventricular (LV) lead 20 extends through one or more veins, the vena cava, right atrium 26, and into the coronary sinus 30 to a region adjacent to the free wall of left ventricle 32 of heart 12. Right atrial (RA) lead 22 extends through one or more veins and the vena cava, and into the right atrium 26 of heart 12.

In some examples, external computing device 24 takes the form of a handheld computing device, computer workstation, networked computing device, smartphone, tablet, or external programmer that includes a user interface for presenting information to and receiving input from a user. A user, such as a physician, technician, surgeon, electrophysiologist, or other clinician, may interact with external computing device 24 to retrieve physiological or diagnostic information from IMD 16. A user may also interact with external computing device 24 to program IMD 16, e.g., select values for operational parameters of the IMD. External computing device 24 may include a processor configured to evaluate EGM signals transmitted from IMD 16 to external computing device 24.

IMD 16 and external computing device 24 may communicate via wireless communication using any techniques known in the art. Examples of communication techniques may include, for example, communication according to the Bluetooth® or BLE protocols. Other communication techniques are also contemplated. External computing device 24 may also communicate with one or more other external devices using a number of known communication techniques, both wired and wireless.

In accordance with the techniques of the disclosure, devices, systems, and methods for establishing a wireless communication session between external computing device 24 and IMD 16 are described. In some examples, IMD 16 implements an advertisement cadence to reduce the power consumption of a wireless radio of IMD 16. The advertisement cadence comprises periods of time wherein IMD 16 is discoverable interleaved with periods of time wherein IMD 16 is non-discoverable. During the periods of time wherein IMD 16 is discoverable, IMD 16 activates its wireless radio and issues advertisements indicating the availability of IMD 16 for a wireless connection. During the periods of time wherein IMD 16 is not discoverable, IMD 16 deactivates its wireless radio to conserve power.

As one example, an example advertisement cadence has a length of X seconds, where X is any number. In one example, the length is about 30 seconds to about 180 seconds. In this example, during a first portion of the advertisement cadence, IMD 16 is discoverable. In some examples, a length of the first portion of the advertisement cadence is Y seconds, where Y is any number less than X. In one example, the length of the first portion is about 453 milliseconds. During this first portion, IMD 16 activates a wireless radio and transmits a plurality of advertisements (e.g., between 2 and 10 advertisements). During a second portion of the advertisement cadence, IMD is not discoverable. In some examples, a length of the first portion of the advertisement cadence is (X-Y) seconds. For example, the length of the second portion is between 29.547 seconds (e.g., 30 seconds-453 milliseconds) and 179.547 seconds (e.g., 180 seconds-453 milliseconds). During this second portion, IMD 16 deactivates its wireless radio to conserve power.

As another example, an example advertisement cadence is an advertisement schedule. In such an example, the periods of time wherein IMD 16 is discoverable and the periods of time wherein IMD 16 is not discoverable may be synchronized with a calendar date and/or time. For example, IMD 16 may be discoverable from 9:00:00 AM GMT to 9:05:00 AM GMT on each Monday of each week, and IMD 16 is not discoverable during all other periods of each week. The techniques of the disclosure may use other advertisement schedules, such as hourly, daily, weekly, bi-weekly, semi-monthly, monthly, bi-monthly, or yearly advertisement schedules. In some examples, a clinician may configure IMD 16 to operate according to a user-defined advertisement schedule having a plurality of periods of time wherein IMD 16 is discoverable and a plurality of periods of time wherein IMD 16 is not discoverable, and wherein each period of plurality of periods of time wherein IMD 16 is discoverable and each of the plurality of periods of time wherein IMD 16 is not discoverable may be different lengths of time.

During a period of time wherein IMD 16 is discoverable, IMD 16 activates its wireless radio and issues one or more advertisements indicating the availability of IMD 16 for a wireless connection. External computing device 24, for example, receives an advertisement from IMD 16 indicating an availability of IMD 16 for a wireless connection. Based on the advertisement, external computing device 24 determines an advertisement cadence for IMD 16. For example, the advertisement may indicate a model type or unique identifier of IMD 16 with which external computing device 24 may use to reference a corresponding advertisement cadence. In other examples, external computing device 24 issues, to IMD 16, a scan request, and receives, from IMD 16, a scan response. In this example, external computing device 24 determines an advertisement cadence for IMD 16 based on the scan response. For example, the scan request may request, from IMD 16, a model type or unique identifier from IMD 16, and the scan response may specify such information.

External computing device 24 issues a request to establish the wireless connection to IMD 16 at a time determined based on the advertisement cadence, such that the wireless connection to IMD 16 is established during one of the periods of time wherein IMD 16 is discoverable. In other words, external computing device 24 issues the request at a time determined to provide sufficient time to initiate and establish the wireless connection to IMD 16 before the period of time wherein IMD 16 is discoverable lapses. The determined time at which external computing device 24 issues the request may be determined to correspond with the Nth time (e.g., first, second, or third time) that IMD 16 repeats the advertisement according to the cadence.

In some examples where the advertisement cadence may be unknown, unavailable, or otherwise unreliable, the techniques of the disclosure may allow for other means of increasing the reliability of establishing a communication session with IMD 16. For example, external computing device 24 determines that a request to establish the wireless connection to IMD 16 has failed. Instead of, or in addition to, determining an advertisement cadence of IMD 16 as described above, external computing device 24 may increase a scanning duty cycle to detect available devices (e.g., increasing a frequency or rate of performing scans for available devices from a baseline frequency or rate of performing such scans for available devices) so as to increase a likelihood that external computing device 24 scans for available devices during a period of time wherein IMD 16 is discoverable. In further examples, external computing device 24 may use the increased scanning duty as a new baseline scanning duty for subsequent scans for available devices. In some examples, each time a connection attempt fails, external computing device 24 may further increase a scanning duty cycle until a wireless connection is successfully established. However, increasing the frequency of the scanning duty cycle of external computing device 24 may increase the power consumption of external computing device 24. In examples where the external computing device is a mobile device, such as a smartphone, increasing the power consumption may negatively affect battery life of the mobile device, which may adversely affect the user. To mitigate the increased power consumption, in some examples, upon successfully establishing the wireless connection, computing device 24 may return to the baseline scanning duty for subsequent scans for available devices.

In other examples, the techniques of the disclosure may be implemented with a peripheral device that is not an IMD. For example, the techniques of the disclosure may enable establishing a low-power connection between an external computing device, which acts as the central device, and another external computing device, which acts as the peripheral device. For example, the techniques of the disclosure may enable establishing a low-power connection between two devices such one or more smart phones, laptop computers, desktop computers, tablets, personal digital assistants (PDAs), headphones, speakers, printers, webcams, keyboards, mice, and other user-input devices, storage devices, hand-held gaming devices, monitors or display devices, wearable devices, and/or GPS devices, one of which acts as a central device and one of which acts as a peripheral device. In other words, the techniques of the disclosure may be applied not only to wireless connections between an external computing device and an IMD, but to wireless connections between any central and peripheral device.

Such techniques as disclosed herein may increase the likelihood that a connection attempt to an IMD succeeds. Furthermore, such techniques as disclosed herein may reduce the length of time required between the discovery of an IMD by an external device and the successful establishment of a wireless connection between the IMD and external device. By reducing the number of failed connections, the techniques disclosed herein may reduce the length of time and/or number of times that the IMD activates its wireless radio, thereby reducing the power usage of the IMD when establishing wireless connections. By reducing the power usage of the IMD using the techniques disclosed herein, an IMD may significantly increase its battery lifetime, thereby reducing the number of IMD maintenance surgeries necessary for the patient to undergo to replace an IMD with depleted battery. In some examples, the techniques of the disclosure may increase the battery lifetime of the IMD by multiple months or even multiple years.

Furthermore, the techniques of the disclosure may reduce the power consumption by the external computing device. In examples where the external computing device is a smartphone of the patient, the techniques of the disclosure may allow for significantly increased connectivity between the IMD and smartphone while preserving the battery capacity of both the IMD and the smartphone. Thus, the systems as disclosed herein may allow for wider adoption of smartphone usage to control therapy of the IMD, which may eliminate the need for a separate external programmer to control therapy of the IMD, thereby reducing the cost to the patient of IMD therapy.

Figure 2:
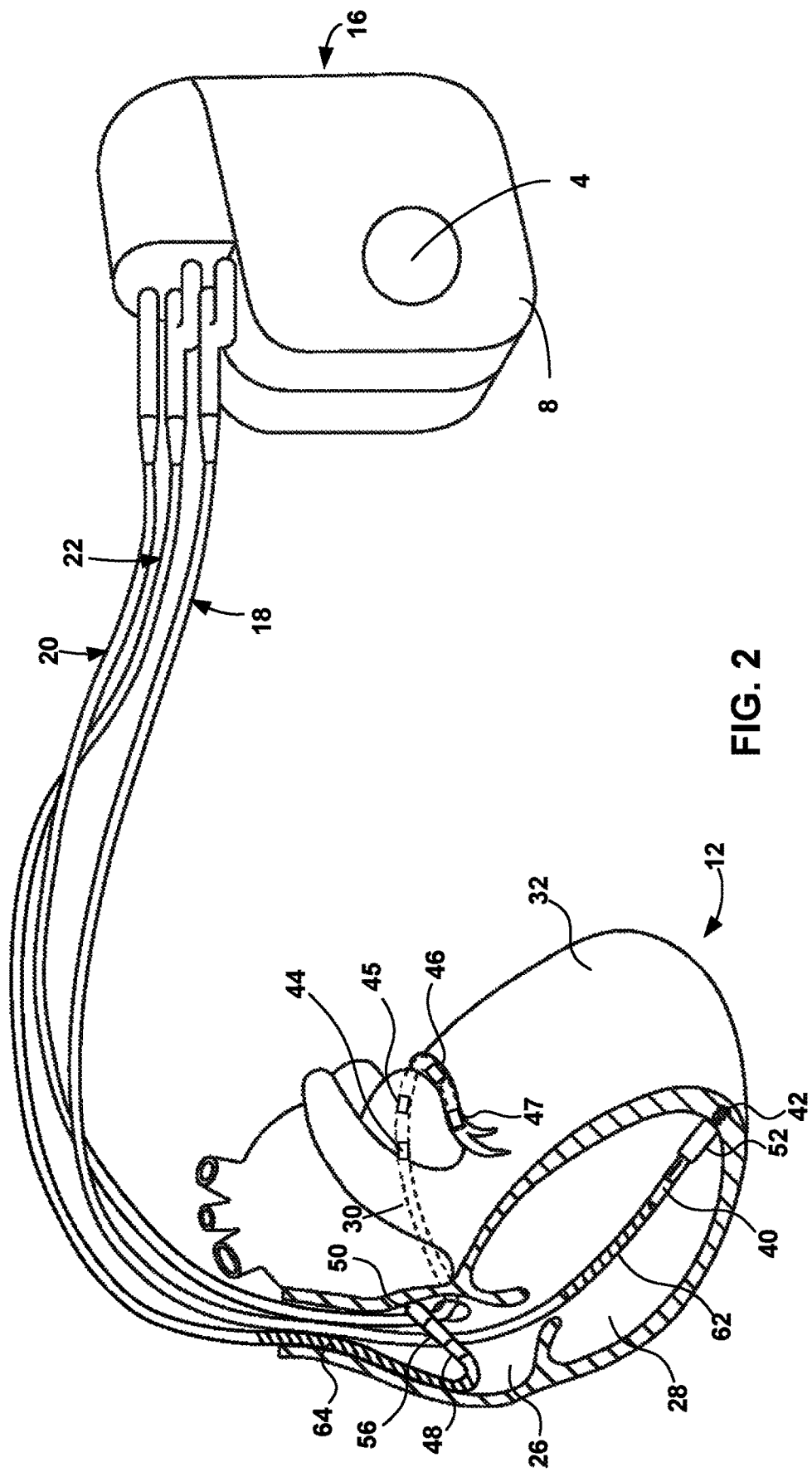
FIG. 2 is a conceptual diagram illustrating the IMD and leads of the system of FIG. 1 in greater detail.

FIG. 2 is a conceptual diagram illustrating IMD 16 and leads 18, 20 and 22 of system 10 in greater detail. In the illustrated example, bipolar electrodes 40 and 42 are located adjacent to a distal end of lead 18, and bipolar electrodes 48 and 50 are located adjacent to a distal end of lead 22. In addition, four electrodes 44, 45, 46 and 47 are located adjacent to a distal end of lead 20. Lead 20 may be referred to as a quadrapolar LV lead. In other examples, lead 20 may include more or fewer electrodes. In some examples, LV lead 20 comprises segmented electrodes, e.g., in which each of a plurality of longitudinal electrode positions of the lead, such as the positions of electrodes 44, 45, 46 and 47, includes a plurality of discrete electrodes arranged at respective circumferential positions around the circumference of lead.

In the illustrated example, electrodes 40 and 44-48 take the form of ring electrodes, and electrodes 42 and 50 may take the form of extendable helix tip electrodes mounted retractably within insulative electrode heads 52 and 56, respectively. Leads 18 and 22 also include elongated electrodes 62 and 64, respectively, which may take the form of a coil. In some examples, each of electrodes 40, 42, 44-48, 50, 62, and 64 is electrically coupled to a respective conductor within the lead body of its associated lead 18, 20, 22 and thereby coupled to circuitry within IMD 16.

In some examples, IMD 16 includes one or more housing electrodes, such as housing electrode 4 illustrated in FIG. 2, which may be formed integrally with an outer surface of hermetically-sealed housing 8 of IMD 16 or otherwise coupled to housing 8. In some examples, housing electrode 4 is defined by an uninsulated portion of an outward facing portion of housing 8 of IMD 16. Other divisions between insulated and uninsulated portions of housing 8 may be employed to define two or more housing electrodes. In some examples, a housing electrode comprises substantially all of housing 8.

Housing 8 encloses a signal generator that generates therapeutic stimulation, such as cardiac pacing, cardioversion, and defibrillation pulses, as well as a sensing module for sensing electrical signals attendant to the depolarization and repolarization of heart 12. Housing 8 may also enclose a memory for storing the sensed electrical signals. Housing 8 may also enclose a telemetry module for communication between IMD 16 and external computing device 24.

IMD 16 senses electrical signals attendant to the depolarization and repolarization of heart 12 via electrodes 4, 40, 42, 44-48, 50, 62, and 64. IMD 16 may sense such electrical signals via any bipolar combination of electrodes 40, 42, 44-48, 50, 62, and 64. Furthermore, any of the electrodes 40, 42, 44-48, 50, 62, and 64 may be used for unipolar sensing in combination with housing electrode 4.

The illustrated numbers and configurations of leads 18, 20 and 22 and electrodes are merely examples. Other configurations, i.e., number and position of leads and electrodes, are possible. In some examples, system 10 may include an additional lead or lead segment having one or more electrodes positioned at different locations in the cardiovascular system for sensing and/or delivering therapy to patient 14. For example, instead of or in addition to intercardiac leads 18, 20 and 22, system 10 may include one or more epicardial or extravascular (e.g., subcutaneous or substernal) leads not positioned within heart 12.

Furthermore, although described herein in the context of example IMD 16, the techniques for establishing wireless communication sessions described herein may be implemented to establish a communication session with any type of implanted or external medical device. As examples, the techniques may be implemented to establish a wireless communication session with a transcatheter pacemaker configured for implantation within the heart, such as the Micra™ transcatheter pacing system commercially available from Medtronic PLC of Dublin Ireland, an insertable cardiac monitor, such as the Reveal LINQ™ ICM, also commercially available from Medtronic PLC, a neurostimulator, a drug delivery device, or a wearable device such as a wearable cardioverter defibrillator, a fitness tracker, or other wearable device.

Figure 3:
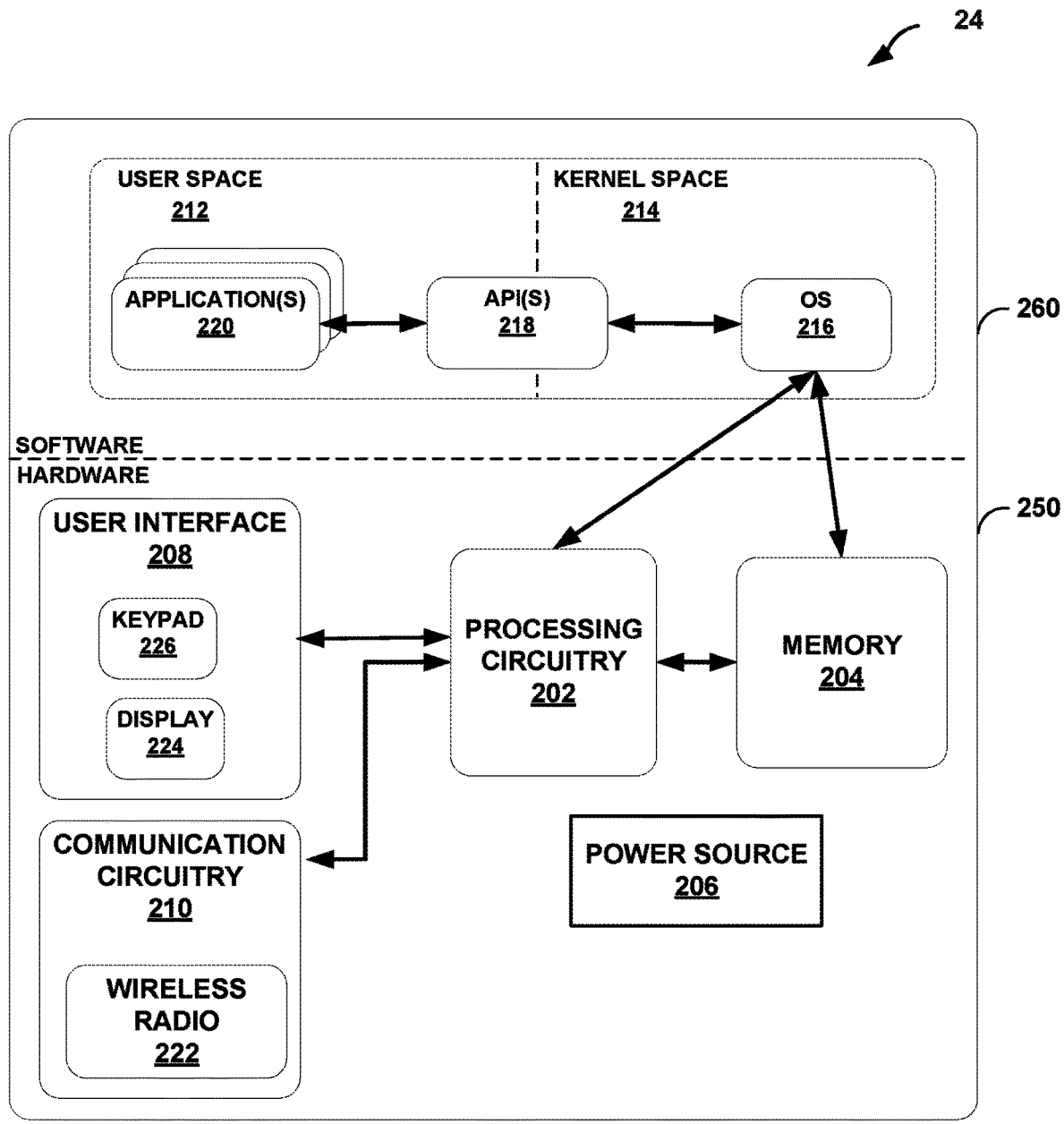
FIG. 3 is a block diagram illustrating an example external computing device in accordance with the techniques of the disclosure.

FIG. 3 is a block diagram illustrating an example external computing device 24 in accordance with the techniques of the disclosure. In some examples, external computing device 24 is a smartphone or an external programmer.

In the example of FIG. 3, external computing device 24 is described as a hardware environment 250 and a software environment 260. However, in some examples, all or a portion of hardware environment 250 may be implemented as software. Further, in some examples, all or a portion of software environment 260 may be implemented as hardware.

Hardware environment 250 includes processing circuitry 202, memory 204, user interface 208, communication circuitry 210, and power source 206. A clinician or patient may interact with processing circuitry 202 via a user interface 208 to, for example, program therapy for patient 12. In other examples, a clinician or patient may interact with processing circuitry 202 to retrieve information from IMD 16, program a monitoring function of processing circuitry 202 or IMD 16, or for other reasons not expressly describe herein. Further, processing circuitry 202 may establish a wireless connection with IMD 16 via wireless radio 222 of communication circuitry 210. Processing circuitry 202 may generate information regarding the wireless connection for presentation to the clinician via user interface 208. User interface 208 may include display 224 and keypad 226 and may also include a touch screen or peripheral pointing devices for receiving input from a user. Processing circuitry 202 may include one or more microprocessors, digital signal processors (DSPs), application specific integrated circuits (ASICs), field programmable gate arrays (FPGAs), or any other equivalent integrated or discrete logic circuitry, as well as any combinations of such components.

External computing device 24 also includes a memory 204. Memory 204 may include program instructions that, when executed by processing circuitry 202, cause external computing device 24 to perform the functions ascribed to external computing device 24 herein. In some examples, memory 204 is random access memory (RAM), read only memory (ROM), programmable read only memory (PROM), erasable programmable read only memory (EPROM), electronically erasable programmable read only memory (EEPROM), flash memory, comprising executable instructions for causing the one or more processors to perform the actions attributed to them. Further, memory 204 may be implanted entirely in hardware, software, or a combination thereof.

Processing circuitry 202 and memory 204 provide an operating environment for a software stack (e.g., software environment 260) that executes one or more application(s) 220 for establishing a wireless connection to IMD 16 such that applications 220 may interact with IMD 16 to, for example, configure one or more operations and functions of IMD 16, upload data from or download data to IMD 16, control therapy of IMD 16, etc. External computing device 24 partitions the virtual and/or physical address space provided by memory 204 into user space 212, allocated for running user processes, and kernel space 214, which is protected and generally inaccessible by user processes. Operating system kernel 216 executes in kernel space 214 and may include, for example, an AndroidTM operating system kernel available from Google, Inc., an iOS™ operating system kernel available from Apple, Inc., a Windows-based operating system kernel, available from Microsoft Corp., or a Linux- or other Unix-variant-based kernel. In other examples, operating system kernel 216 may include another type of operating system kernel not expressly described herein.

Communication circuitry 210 includes any suitable circuitry, firmware, software, or any combination thereof for communicating with another device, such as IMD 16 of FIG. 1. For example, communication circuitry 210 may include wireless radio 222, one or more antennae, transmitters, receivers, modulation and demodulation circuitry, filters, amplifiers, or the like for radio frequency communication with other devices, such as external device 24. Under the control of processing circuitry 202, communication circuitry 210 may receive downlinked data from and send uplinked data to IMD 16 with the aid of wireless radio 222, which may include at least one antenna, which may be internal and/or external. Processing circuitry 202 may provide the data to be uplinked to IMD 16 and the control signals for wireless radio 222 within communication circuitry 210, e.g., via an address/data bus. In some examples, communication circuitry 210 may provide received data to processing circuitry 202 for processing or to memory 204 for storage.

In one example, applications 220 execute in user space 212 to communicate with IMD 16. Applications 220 may invoke one or more Application Programming Interfaces (APIs) 218 to communicate with operating system 216. APIs 218 may execute in user space 212, kernel space 214, or a combination of kernel space 214 and user space 212. For example, applications 220 may invoke a wireless communication API of APIs 218 to establish a wireless communication session with IMD 16. In some examples, the wireless communication API of APIs 218 is a Bluetooth® or BLE API. The wireless communication API of APIs 218 may provide a library of functions that, when used, cause operating system 216 to control communication circuitry 210 and wireless radio 222 of hardware environment 250 to establish the wireless communication session with IMD 16.

In some examples, operating system 216 is a version of Android™ OS and API 218 is a Bluetooth® or BLE API. Further description regarding the implementation of the Bluetooth® protocol in Android™ OS is provided in Bluetooth, Android™ Developers, available at https://developer.android.com/guide/topics/connectivity/bluetooth.html (retrieved Apr. 23, 2018), the entire content of which is incorporated herein by reference. Further description regarding the implementation of the BLE protocol in Android™ OS is provided in Bluetooth Low Energy, Android™ Developers, available at https://developer.android.com/guide/topics/connectivity/bluetooth-le.html (retrieved Apr. 23, 2018), the entire content of which is incorporated herein by reference.

In some examples, OS 216 is a version of Apple iOS™ and API 218 is a Bluetooth® or BLE API. Further description regarding the implementation of the Bluetooth protocol in Apple iOS™ is provided in About Core Bluetooth, Apple Inc., available at https://developer.apple.com/library/content/documentation/NetworkingInternetWeb/Conceptual/CoreBluetooth_concepts/AboutCoreBluetooth/Introduction.html (retrieved Apr. 23, 2018), the entire content of which is incorporated herein by reference. Further description regarding the implementation of the BLE protocol in Apple iOS™ is provided in Core Bluetooth, Apple Developer Documentation, Apple Inc., available at https://developer.apple.com/documentation/corebluetooth (retrieved Apr. 23, 2018), the entire content of which is incorporated herein by reference. In other examples, OS 216 is a Windows-based operating system kernel, available from Microsoft Corp., a Linux- or other Unix-variant-based kernel, or another type of operating system kernel not expressly described herein.

In one example, application 220 issues a request to API 218 to discover available peripheral devices. API 218 passes the request to operating system 216, and in response, perform a scan for discoverable devices. For example, communication circuitry 210 and wireless radio 222 listen for advertisements issued by one or more discoverable peripheral devices. Communication circuitry 210 and wireless radio 222 receive, from IMD 16, an advertisement indicating an availability of IMD 16 for a wireless connection.

In response to receiving the advertisement, operating system 216 creates an object handle which API 218 passes to application 220. The object handle is an abstraction of IMD 16 that application 220 may use to establish a wireless connection. The object handle may be a constant that application 220 may use across multiple periods of time wherein IMD 16 is discoverable and periods of time wherein IMD 16 is non-discoverable. For example, the object handle may include one or more characters, numbers, or symbols that allow application 220 to identify, to operating system 216, the specific device to which a connection is sought to be established. In some examples, the object handle is a unique 16-bit identifier. In some examples, the object handle is a unique device address. In examples where application 220 connects to a plurality of peripheral devices (e.g., one or more IMDs, such as IMD 16, wearable devices, computing devices, or other peripheral devices), operating system 216 creates a unique object handle for each peripheral device of the plurality of peripheral devices.

As operating system 216 receives the advertisement, creates the object handle for IMD 16, and passes the object handle to application 220 via APIs 218, an implied latency occurs before application 220 may issue a connection request back through operating system 216 and hardware environment 250 to IMD 16. This combined latency occurs while IMD 16 is waiting for external computing device 24 to request establishment of a communication session. If the latency is longer than remaining period of time wherein IMD 16 is discoverable, then IMD 16 may deactivate its wireless radio before the connection may be established. As described above, this may result in repeated and/or unreliable attempts at establishing a wireless communication session, which may inefficiently consume power of both IMD 16 and external computing device 24.

In accordance with the techniques of the disclosure, systems, devices, and methods are disclosed for establishing a communication session with IMD 16 that may provide reduced power consumption and increased reliability over conventional techniques. In one example, during a period of time wherein IMD 16 is discoverable, operating system 216 receives, via wireless radio 222, an advertisement from IMD 16 indicating an availability of IMD 16. In some examples, the advertisement includes unique identifying information for IMD 16. In some examples, the unique identifying information includes a media access control (MAC) address, a device identifier, a lot number, a software version, or a model of IMD 16.

In response to receiving the advertisement, operating system 216 creates an object handle corresponding to IMD 16. In some examples, the object handle includes the unique identifying information for IMD 16. Application 220 receives, via APIs 218, the object handle corresponding to IMD 16. Application 220 determines, based on the object handle, an advertisement cadence for the IMD. For example, application 220 may examine the unique identifying information for IMD 16 to determine the advertisement cadence for a model or software version of IMD 16. In some examples, memory 204 may store a look-up table or other data structure of identifying information for one or more IMDs and corresponding advertisement cadences. Application 220 may cross reference the unique identifying information for IMD 16 to retrieve an advertisement cadence corresponding to IMD 16 in the look-up table.

Conventionally, an operating system may create a unique object handle for each communication session. For example, upon termination of the communication session, or upon failure to establish the communication session, the conventional operating system may destroy the corresponding object handle. However, in accordance with the techniques of the disclosure, the object handle as described herein may persist after a communication session ends or upon a failure to establish the communication session. Thus, application 220 may reuse the same object handle to communicate with a specific device, thereby allowing application 220 to identify the advertisement cadence of IMD 16 upon receipt of an advertisement, even if IMD 16 subsequently becomes non-discoverable before application 220 establishes a wireless connection to IMD 16.

Based on the determined advertisement cadence for IMD 16, application 220 determines a time at which to issue, to operating system 216, a request to establish the wireless connection to the IMD. For example, application 220 may determine, based on the determined advertisement cadence, an upcoming, e.g., the next, period of time wherein IMD 16 is discoverable. In further examples, application 220 may additionally determine a period of time (e.g., a latency) required by operating system 216 to initiate and establish a wireless connection to IMD 16. For example, application 220 may determine one or more of a version of operating system 216, a configuration of processing circuitry 202 and/or memory 204, or a model of external computing device 24 to determine a latency for a specific configuration of external computing device 24. In another example, application 220 may instead use a predetermined period of time instead of directly determining the latency required by operating system 216 to initiate and establish a wireless connection to IMD 16.

Application 220 issues, using the object handle and to APIs 218, the request to establish the wireless connection to IMD 16 at the time determined based on the advertisement cadence. In some examples, application 220 the request to establish the wireless connection to IMD 16 at a time determined based on both the advertisement cadence and the latency of operating system 216. For example, the request to establish the wireless connection to IMD 16 may include the object handle so as to specify, to operating system 216, that IMD 16 is the device with which to establish a connection. In this way, application 220 may align the time required by operating system 216 to initiate and establish the wireless connection to IMD 16 such that operating system 216 establishes the wireless connection to IMD 16 during one of the periods of time wherein IMD 16 is discoverable. Furthermore, application 220 may take into account the time required by operating system 216 to initiate and establish the wireless connection to IMD 16 such that latency due to operating system 216 does not result in sending a connection request to IMD 16 after IMD 16 becomes non-discoverable. Thus, operating system 216 maintains the object handle for IMD 16 even in the absence of an established wireless connection, and application 220 selectively attempts to connect to IMD 16 on the advertisement cadence of IMD 16. By using the unique identifying information specified by the advertisement from IMD 16, application 220 may determine the advertisement cadence in advance of attempting to establish the wireless connection with IMD 16 such that the completion of the connection attempt may be aligned with a period of time wherein IMD 16 is discoverable.

Typically, a clock of IMD 16 and a clock of external computing device 24 are asynchronous with respect to one another, and therefore the exact timing of the issuance of an advertisement by IMD 16 with respect to external computing device 24 is imprecise. However, the advertising duration of IMD 16 is reasonably long enough such that external computing device 24 is not required to connect on a precise boundary. As described in further detail below with respect to FIG. 5, in some examples, the techniques of the disclosure may be implemented where the clock of IMD 16 and the clock of external computing device 24 are asynchronous with respect to one another. Additionally, as described in further detail below with respect to FIG. 6, in some examples, the techniques of the disclosure may be implemented where the clock of IMD 16 and the clock of external computing device 24 are synchronous with respect to one another.

In some examples, operating system 216 receives the advertisement from IMD 16 and establishes the connection with IMD 16 during the same period of time wherein IMD 16 is discoverable. In other examples, operating system 216 receives the advertisement from IMD 16 during a first period of time wherein IMD 16 is discoverable and establishes the connection with IMD 16 during a second period of time wherein IMD 16 is discoverable, wherein at least one period of time wherein IMD 16 is non-discoverable (and in some examples one or more periods wherein IMD 16 is discoverable) is in between the first and second periods of time wherein IMD 16 is discoverable.

In other examples, operating system 216 detects a first discovery sequence of IMD 16 (e.g., by receiving a first advertisement indicating the availability of IDM 14). In response to receiving the advertisement, operating system 216 and application 220 attempt to immediately connect to IMD 16. If the connection attempt fails (e.g., operating system 216 times out the connect request from application 220), operating system 216 preserves the object handle of IMD 16 from the first discovery sequence. Because IMD 16 is already associated with operating system 216 using the object handle, and because application 220 may determine the advertisement cadence of IMD 16 based on the unique identifying information within the first advertisement, it is unnecessary for external computing device 24 to perform a second scan and connection sequence. Therefore, it may only be necessary for application 220 to issue, to operating system 216 and via the preserved object handle, a request to establish the wireless connection with IMD 16 during the next period of time wherein IMD 16 is discoverable. In some examples, external device 24 may deactivate communication circuitry 210 to conserve power during the period of time that IMD 16 is not discoverable. In other examples, external device 24 may application 220 may connect to other peripheral devices during the period of time that IMD 16 is not discoverable.

Upon establishing the connection, external computing device 24 may control one or more operations of IMD 16. For example, a clinician or patient may use external computing device 24 to configured therapy provided by IMD 16 or adjust one or more parameters of the therapy provided by IMD 16. As another example, a clinician or patient may use external computing device 24 to upload data to or download data from IMD 16. In other examples, a clinician or patient may use external computing device 24 to program sensing functionally, collect telemetry and/or status information, or control other operations of IMD 16.

Accordingly, such techniques as disclosed herein may increase the likelihood that a connection attempt by operating system 216 to IMD 114 succeeds. By reducing the number of failed connections, the techniques disclosed herein may reduce the length of time and/or number of times that IMD 16 activates its wireless radio, thereby reducing the power usage of the IMD when establishing wireless connections. Furthermore, such techniques as disclosed herein may reduce the length of time required between the discovery of IMD 114 by operating system 216 and the successful establishment of a wireless connection between IMD 114 and application 220. Such techniques may be particularly useful where IMD 114 must convey time-sensitive or critical information to application 220. A further benefit from the techniques of the disclosure is that the disclosed techniques may be implemented without requiring a change to a pre-existing IMD that is already implanted within a patient. For example, wherein an advertising period of a pre-existing IMD is sufficiently long enough to permit wireless connection via an advertisement cadence scheme, wherein the advertisement cadence is known ahead of time or may be determined by the external computing device, and assuming reasonable clock drift between the IMD and external computing device, the techniques of the disclosure may be applied to pre-existing IMDs to provide increased battery life without requiring that a new IMD be implanted within the patient.

Figure 4:
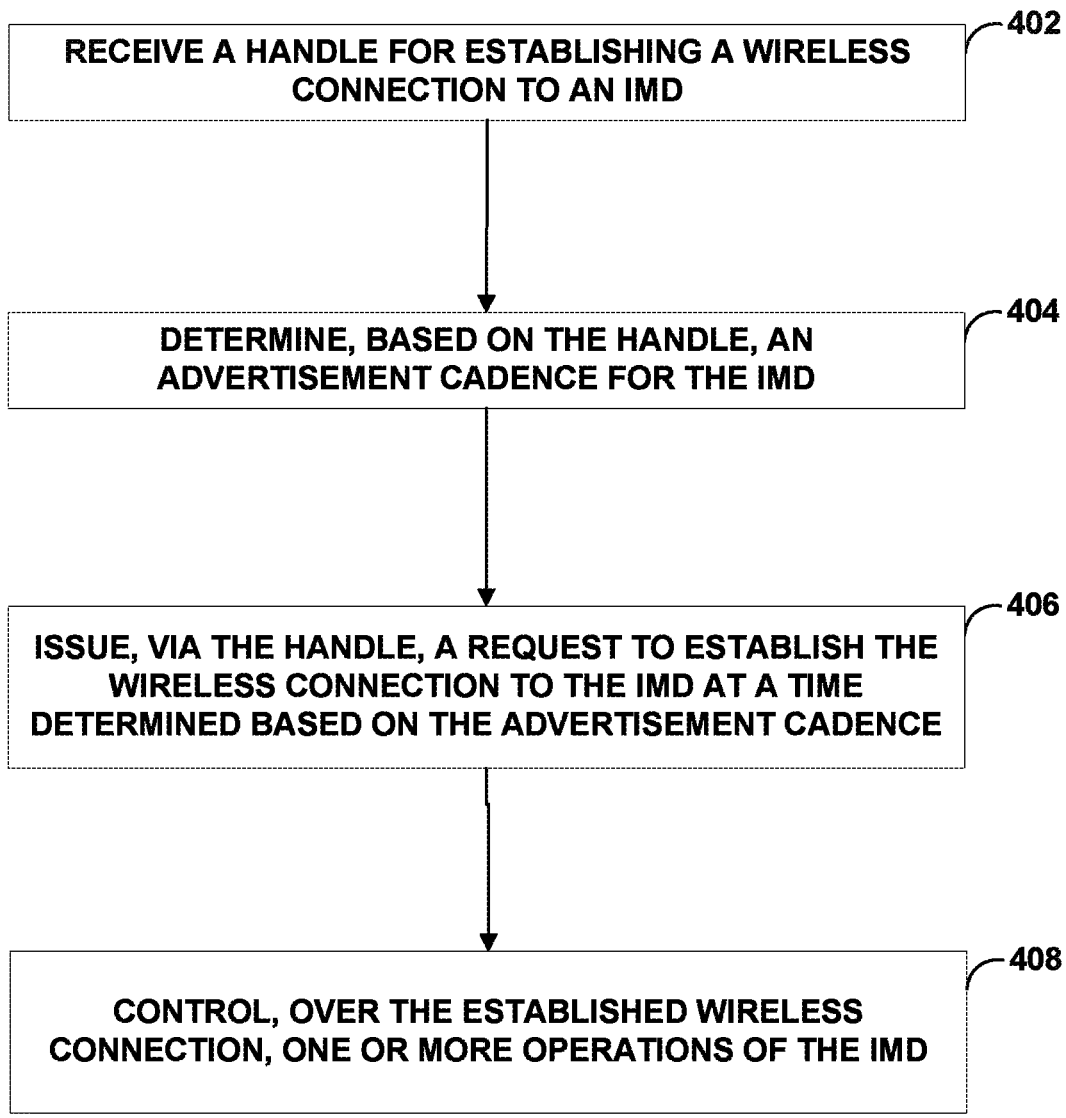
FIG. 4 is a flowchart illustrating an example operation in accordance with the techniques of the disclosure.

FIG. 4 is a flowchart illustrating an example operation in accordance with the techniques of the disclosure. FIG. 4 is described with respect to FIGS. 1 and 3 for convenience.

In the example of FIG. 4, operating system 216 receives, via wireless radio 222 and from IMD 16, an advertisement indicating an availability of IMD 16 for a wireless connection. In response to the advertisement, operating system 216 creates an object handle corresponding to IMD 16. The object handle is an abstraction of IMD 16 that an application, such as application 220, may use to establish a wireless connection to IMD 16. In some examples, the object handle includes unique identifying information for IMD 16. In some examples, the unique identifying information includes a MAC address, a device identifier, a lot number, a software version, or a model of IMD 16. In some examples, operating system 216 may use such unique identifying information to generate the object handle. Application 220 receives, from API 218, the object handle for establishing the wireless connection to IMD 16 (402).

Application 220 determines, based on the object handle, an advertisement cadence for IMD 16 (404). For example, application 220 may examine the unique identifying information of the object handle to determine an advertisement cadence for a model or software version corresponding to IMD 16. In some examples, memory 204 may store a look-up table or other data structure of identifying information for one or more IMDs and corresponding advertisement cadences. In this example, application 220 may cross reference the unique identifying information of the object handle to retrieve an advertisement cadence corresponding to IMD 16 from the look-up table.

In some examples, in parallel to operation 404, operating system 216 may immediately attempt to establish a connection to IMD 16 using conventional techniques. If such an operation succeeds, application 220 may proceed directly to control, over the established wireless connection, one or more operations of IMD 16. However, the remainder of the operations described herein assume that such an attempt fails or is not performed to conserve energy in case the attempt fails.

Based on the determined advertisement cadence for IMD 16, application 220 determines a time at which to issue, to operating system 216, a request to establish the wireless connection to the IMD. For example, application 220 may determine, based on the determined advertisement cadence, the next period of time wherein IMD 16 is discoverable. Application 220 issues, using the object handle and to API 218, the request to establish the wireless connection to IMD 16 at the time determine based on the advertisement cadence (406). In this way, application 220 may align the time required by operating system 216 to initiate and establish the wireless connection to IMD 16 such that operating system 216 establishes the wireless connection to IMD 16 during one of the periods of time wherein IMD 16 is discoverable. Thus, by using the unique identifying information specified by the advertisement from IMD 16, application 220 may determine the advertisement cadence in advance of attempting to establish the wireless connection with IMD 16 such that the completion of the connection attempt may be aligned with a period of time wherein IMD 16 is discoverable.

In response to establishing the wireless connection, application 220 controls, over the established wireless connection, one or more operations of IMD 16 (408). For example, such operations may include beginning, pausing, or suspending delivery of therapy by IMD 16, uploading data to or downloading data from IMD 16, retrieving telemetry or patient status information from IMD 16, etc. Such operations may additionally include adjusting one or more parameters of the therapy delivered by IMD 16. Such operations may further include beginning or stopping the collection of information regarding therapy provided by IMD 16, such as, for example, data related to patient physiological parameters and/or data related to an operational history of IMD 16. Further, such operations may include uploading, to external computing device 24, the information collected by IMD 16.

Figure 5:
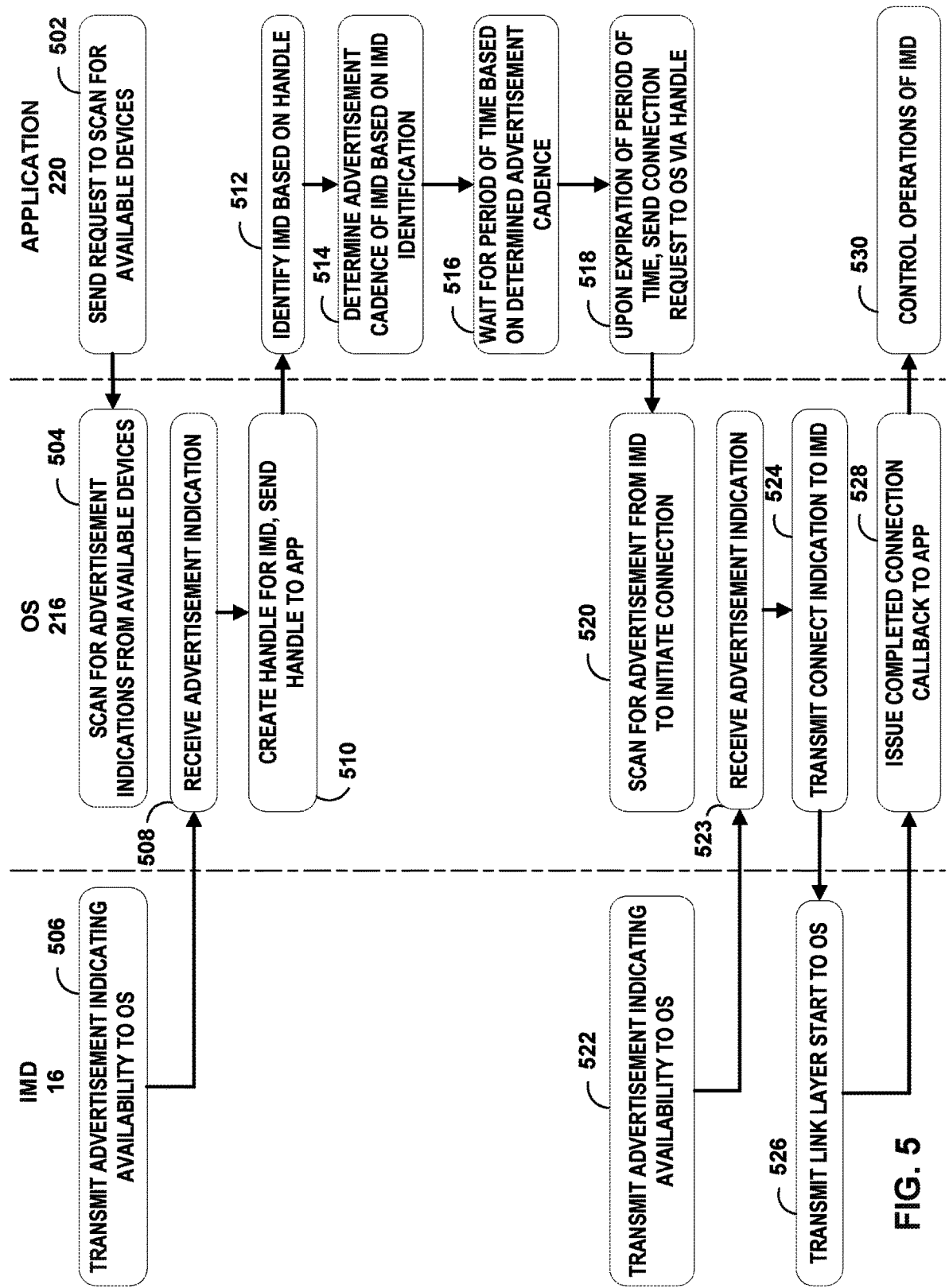
FIG. 5 is a flowchart illustrating an example operation in accordance with the techniques of the disclosure.

FIG. 5 is a flowchart illustrating an example operation in accordance with the techniques of the disclosure. FIG. 5 is described with respect to FIGS. 1 and 3 for convenience.

In one example, external computing device 24 and IMD 16 implement a BLE protocol. In such an example, each of external computing device 24 and IMD 16 implement a state machine comprising five states: standby, advertising, scanning (e.g., active or passive), initiating, and connection (e.g., central or peripheral). A peripheral device, such as IMD 16, implements an advertisement cadence to alternate between periods of time wherein the peripheral device is discoverable (e.g., the advertising state) interleaved with periods of time wherein the peripheral device is non-discoverable (e.g., the standby state). During a period of time that the peripheral device is discoverable, the peripheral device, such as IMD 16, advertises (e.g., transmits) an advertising packet on an advertising channel to indicate an availability of the device for a wireless connection. During a period of time wherein the peripheral device is non-discoverable, the peripheral device, such as IMD 16, deactivates its wireless radio to conserve power (e.g., operates in standby).

While scanning, a central device, such as external computing device 24, monitors an advertisement channel for one or more advertisement packets to discover available devices but without creating a wireless connection to discovered available devices. In response to detecting an advertisement (and, for example, in response to receiving a selection from a user of a device with which to establish a connection), the central device transitions to the initiating state. While initiating, a central device, such as external computing device 24, monitors an advertisement channel for one or more advertisement packets to discover an available device and form a connection to the available device. While connecting, the central device (e.g., initiator) establishes a connection with the peripheral device (e.g., the advertiser).

In the example of FIG. 5, a clock of IMD 16 and a clock of external computing device 24 are asynchronous with respect to one another. Thus, external computing device 24 may first scan for an advertisement from IMD 16 both to identify IMD 16 and determine an advertisement cadence for IMD 16, as well as to identify a first advertisement period of IMD 16. For example, external computing device 24 may identify IMD 16 based on a unique identifier contained within the advertisement received from IMD 16. For example, external computing device 24 may use the unique identifier to reference, from a look-up table stored in memory 204, a corresponding advertising cadence for the IMD specified by the unique identifier. Thereafter, external computing device may attempt to connect to IMD 16 during a subsequent advertisement period of IMD 16.

In another example, external computing device 24 may determine an advertisement cadence of IMD 16 based on a frequency of received advertisements. For example, external computing device 24 may monitor advertisements received from IMD 16 over a period of time. External computing device 24 may determine periods of time wherein IMD 16 is discoverable based on the receipt of advertisements from IMD 16. Similarly, external computing device 24 may determine periods of time wherein IMD 16 is non-discoverable if no advertisements are received. Based on the determination of the periods of time wherein IMD 16 is discoverable and periods of time wherein IMD 16 is non-discoverable, external computing device 24 may reconstruct the advertisement cadence. Thereafter, external computing device may attempt to connect to IMD 16 during a subsequent advertisement period of IMD 16.

In one example, application 220 presents, via user interface 208, an option to scan for available devices. In response to selection, by the user, of the option to scan for available devices, application 220 sends a request to operating system 216 to scan for available devices (502). In other examples, application 220 may automatically send the request to operating system 216 to scan for available devices on a periodic basis. Operating system 216 receives the request and scans an advertisement channel for available devices with which to establish a wireless connection (504). IMD 16 transmits, over the advertisement channel, an advertisement indicating an availability of IMD 16 for a wireless connection (506). Operating system 216 receives, via wireless radio 222, the advertisement from IMD 16 (508).

In response to the advertisement, operating system 216 creates an object handle corresponding to IMD 16 and sends the object handle to application 220 (510). In some examples, the object handle is an abstraction of IMD 16 that application 220 may use to establish a wireless connection to IMD 16. In some examples, the object handle includes unique identifying information for IMD 16. For example, the unique identifying information may include a MAC address, a device identifier, a lot number, a software version, or a model of IMD 16.

Application 220 receives, from API 218, the object handle for establishing the wireless connection to IMD 16. Application 220 identifies IMD 16 based on the handle (512). In some examples, memory 204 may store a look-up table or other data structure of identifying information for one or more handles and model or software versions corresponding to peripheral devices. Application 220 may use the handle to reference the look-up table to retrieve a corresponding model or software version of IMD 16 that corresponds to the handle. Further, application 220 determines an advertisement cadence of IMD 16 based on the identification of IMD 16 (514). For example, application 220 may examine the unique identifying information of the object handle to determine an advertisement cadence for a model or software version corresponding to IMD 16. In some examples, memory 204 may store a look-up table or other data structure of identifying information for one or more IMDs and corresponding advertisement cadences. In this example, application 220 may cross reference the unique identifying information of the object handle to retrieve an advertisement cadence corresponding to IMD 16 from the look-up table.

In some examples, in parallel to operations 512 and 514, operating system 216 may immediately attempt to establish a connection to IMD 16 using conventional techniques. If such an operation succeeds, application 220 may proceed directly to control, over the established wireless connection, one or more operations of IMD 16. However, the remainder of the operations described herein assume that such an attempt fails or is not performed to conserve energy in case the attempt fails.

Based on the determined advertisement cadence for IMD 16, application 220 determines a time at which to issue, to operating system 216, a request to establish the wireless connection to the IMD. For example, application 220 may determine, based on the determined advertisement cadence, the next period of time wherein IMD 16 is discoverable. In some examples, application 220 waits for a period of time based on the determined advertisement cadence (516). Upon expiration of the period of time, application 220 sends, using the object handle, a connection request to operating system 518 to initiate a wireless connection with IMD 16 (518).

In response to the connection request, operating system 216 attempts to initiate a wireless connection with IMD 16. Operating system 216 scans for an advertisement from IMD 16 indicating an availability of IMD 16 for a connection (520). IMD 16 transmits, over the advertisement channel, an advertisement indicating an availability of IMD 16 for a wireless connection (522). In response to receiving the advertisement (523), operating system 216 transmits, via wireless radio 222, a "connect" indication to IMD 16 (524). In some examples, operating system 216 may directly control one or more aspects of communication circuitry 210 to transmit and receive communications to and from IMD 16. In other examples, operating system 216 may use one or more APIs 218 to control one or more aspects of communication circuitry 210 to transmit and receive communications to and from IMD 16. In response to receiving the "connect" indication from operating system 216, IMD 16 transmits a "link layer start" indication to operating system 216 (526). The "link layer start" indication indicates to operating system 216 that the wireless connection to IMD 16 has completed and the connection is available for transporting data. In response to receiving the "link layer start" indication from IMD 16, operating system 216 issues a callback to application 220 via API 218 that the wireless connection to IMD 16 has completed (528). In response to receiving the callback, application 220 may control, over the established wireless connection, one or more operations of IMD 16 (530).

Thus, because application 220 has determined the advertisement cadence of IMD 16, application 220 may align the initiating step of operating system 216 with one of the periods of time wherein IMD 16 is discoverable (e.g., during a scanning period of IMD 16) such that operating system 216 may establish the wireless connection while IMD 16 is discoverable. Thus, such techniques as disclosed herein may increase the likelihood that a connection attempt succeeds and/or the reliability of establishing the wireless connection, thereby reducing the power usage of the IMD when establishing wireless connections. By reducing the power usage of the IMD using the techniques disclosed herein, an IMD may have increased battery lifetime, thereby reducing the number of IMD maintenance surgeries necessary for the patient to undergo. Furthermore, such techniques as disclosed herein may reduce the length of time required between the discovery of an IMD by an external device and the successful establishment of a wireless connection between the IMD and external device. Such techniques may be particularly useful where an IMD must convey time-sensitive or critical information to the external device.

Figure 6:
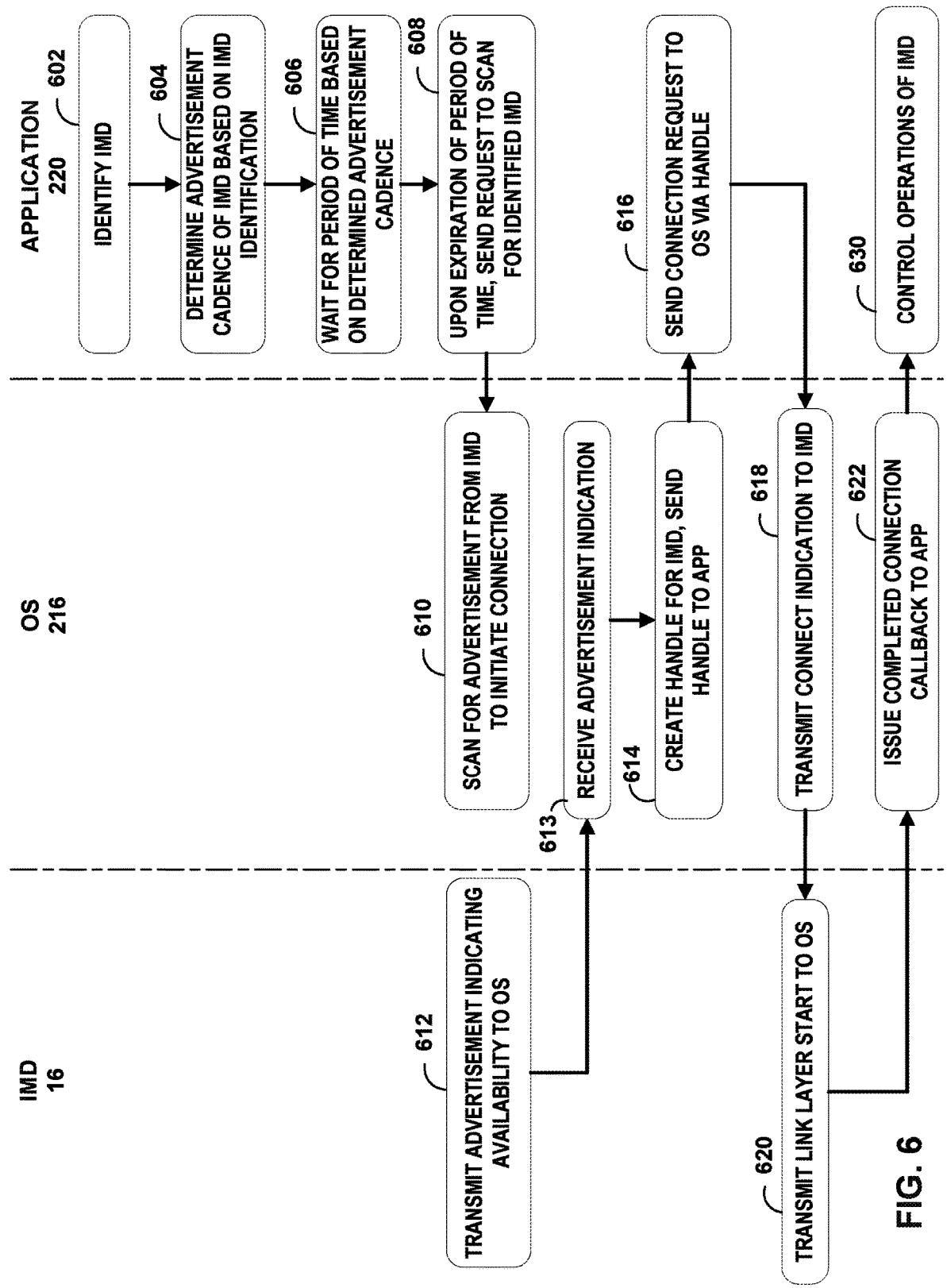
FIG. 6 is a flowchart illustrating an example operation in accordance with the techniques of the disclosure.

FIG. 6 is a flowchart illustrating an example operation in accordance with the techniques of the disclosure. FIG. 6 is described with respect to FIGS. 1 and 3 for convenience.

In the example of FIG. 6, a clock of IMD 16 and a clock of external computing device 24 are synchronous with respect to one another. Thus, external computing device may predetermine both an advertisement cadence for a preselected IMD 16 and predetermine a timing of a first advertisement period of IMD 16, and attempt to connect to IMD 16 during the first advertisement period.

In the example of FIG. 6, application 220 selects a predetermined IMD 16 (602). For example, application 220 may receive, from a clinician via user interface 208, an identification of a specific IMD 16 with which to establish a wireless connection. In some examples, application 220 receives, via user interface 208, unique identifying information for IMD 16, such as a MAC address, a device identifier, a lot number, a software version, or a model of IMD 16.

Application 220 determines an advertisement cadence of IMD 16 based on the identification of IMD 16 (604). For example, application 220 may examine the received unique identifying information to determine an advertisement cadence for a model or software version corresponding to IMD 16. In some examples, memory 204 may store a look-up table or other data structure of identifying information for one or more IMDs and corresponding advertisement cadences. In this example, application 220 may cross reference the unique identifying information for IMD 16 to retrieve an advertisement cadence corresponding to IMD 16 from the look-up table.

In some examples, in parallel to operation 604, operating system 216 may immediately attempt to establish a connection to IMD 16 using conventional techniques. If such an operation succeeds, application 220 may proceed directly to control, over the established wireless connection, one or more operations of IMD 16. However, the remainder of the operations described herein assume that such an attempt fails or is not performed to conserve energy in case the attempt fails.

Based on the determined advertisement cadence for IMD 16, application 220 determines a time at which to issue, to operating system 216, a request to establish the wireless connection to IMD 16. For example, application 220 may determine, based on the determined advertisement cadence, the next period of time wherein IMD 16 is discoverable. In some examples, application 220 waits for a period of time based on the determined advertisement cadence (606). Upon expiration of the period of time, application 220 sends a request to operating system 216 to scan for the identified device (e.g., IMD 16) (608). Operating system 216 receives the request and scans an advertisement channel for the identified device with which to establish the wireless connection (610). IMD 16 transmits, over the advertisement channel, an advertisement indicating an availability of IMD 16 for a wireless connection (612). In response to receiving the advertisement (613), operating system 216 creates an object handle corresponding to IMD 16 and sends the object handle to application 220 (614). In some examples, the object handle is an abstraction of IMD 16 that application 220 may use to establish the wireless connection to IMD 16. Application 220 sends, using the object handle, a connection request to operating system 518 to initiate the wireless connection with IMD 16 (616).

In response to the connection request, operating system 216 attempts to initiate the wireless connection with IMD 16. Operating system 216 transmits, via wireless radio 222, a "connect" indication to IMD 16 (618). In some examples, operating system 216 may directly control one or more aspects of communication circuitry 210 to transmit and receive communications to and from IMD 16. In other examples, operating system 216 may use one or more APIs 218 to control one or more aspects of communication circuitry 210 to transmit and receive communications to and from IMD 16. In response to receiving the "connect" indication from operating system 216, IMD 16 transmits a "link layer start" indication to operating system 216 (620). The "link layer start" indication indicates to operating system 216 that the wireless connection to IMD 16 has completed and the connection is available for transporting data. In response to receiving the "link layer start" indication from IMD 16, operating system 216 issues a callback to application 220 that the wireless connection to IMD 16 has completed (622). In response to receiving the callback, application 220 may control, over the established wireless connection, one or more operations of IMD 16.

Thus, because application 220 shares a synchronized clock with IMD 16, application 220 may predetermine an advertisement cadence of IMD 16. Furthermore, based on the advertisement cadence, application 220 may align the initiating step of operating system 216 with one of the periods of time wherein IMD 16 is discoverable (e.g., during a scanning period of IMD 16) such that operating system 216 may establish the wireless connection while IMD 16 is discoverable. Thus, such techniques as disclosed herein may increase the likelihood that a connection attempt succeeds and/or the reliability of establishing the wireless connection, thereby reducing the power usage of the IMD when establishing wireless connections. By reducing the power usage of the IMD using the techniques disclosed herein, an IMD may have increased battery lifetime, thereby reducing the number of IMD maintenance surgeries necessary for the patient to undergo. Furthermore, such techniques as disclosed herein may reduce the length of time required between the discovery of an IMD by an external device and the successful establishment of a wireless connection between the IMD and external device. Such techniques may be particularly useful where an IMD must convey time-sensitive or critical information to the external device.

The techniques described in this disclosure may be implemented, at least in part, in hardware, software, firmware or any combination thereof. For example, various aspects of the described techniques may be implemented within one or more processors, including one or more microprocessors, digital signal processors (DSPs), application specific integrated circuits (ASICs), field programmable gate arrays (FPGAs), or any other equivalent integrated or discrete logic circuitry, as well as any combinations of such components. The term "processor" or "processing circuitry" may generally refer to any of the foregoing logic circuitry, alone or in combination with other logic circuitry, or any other equivalent circuitry. A control unit comprising hardware may also perform one or more of the techniques of this disclosure.

Such hardware, software, and firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components or integrated within common or separate hardware or software components.

The techniques described in this disclosure may also be embodied or encoded in a non-transitory computer-readable medium, such as a computer-readable storage medium, containing instructions. Instructions embedded or encoded in a non-transitory computer-readable storage medium may cause a programmable processor, or other processor, to perform the method, e.g., when the instructions are executed. Non-transitory computer readable storage media may include random access memory (RAM), read only memory (ROM), programmable read only memory (PROM), erasable programmable read only memory (EPROM), electronically erasable programmable read only memory (EEPROM), flash memory, a hard disk, a CD-ROM, a floppy disk, a cassette, magnetic media, optical media, or other computer readable media.

Various examples have been described. These and other examples are within the scope of the following claims.

What is claimed is:
1. A method comprising:
  receiving, by an application executing on an operating system executing on processing circuitry of an external computing device, an object handle for establishing a wireless connection to a peripheral device of a plurality of peripheral devices, wherein the operating system creates the object handle to identify the peripheral device from other peripheral devices of the plurality of peripheral devices;
  determining, by the application and based on the object handle, an advertisement cadence for the peripheral device, wherein the advertisement cadence comprises periods of time wherein the peripheral device is discoverable interleaved with periods of time wherein the peripheral device is non-discoverable; and at a time determined based on the advertisement cadence, issuing, by the application and using the object handle, a request to the operating system to establish the wireless connection to the peripheral device, such that the operating system establishes the wireless connection to the peripheral device during one of the periods of time wherein the peripheral device is discoverable.

2. The method of claim 1, further comprising determining, by the application, an amount of time required by the operating system to establish the wireless connection to the peripheral device, and
wherein issuing the request to the operating system to establish the wireless connection to the peripheral device comprises issuing the request that to the operating system to establish the wireless connection to the peripheral device at a time determined based on the advertisement cadence and the amount of time required by the operating system to establish the wireless connection to the peripheral device, such that the operating system establishes the wireless connection to the peripheral device during one of the periods of time wherein the peripheral device is discoverable.

3. The method of claim 2, wherein determining the amount of time required by the operating system to establish the wireless connection to the peripheral device comprises determining the amount of time required by the operating system to establish the wireless connection to the peripheral device based on at least one of:
a version of the operating system;
a configuration of the processing circuitry; or
a model of the external computing device.

4. The method of claim 1,
wherein receiving the object handle for establishing the wireless connection to the peripheral device comprises receiving, from an Application Program Interface (API) for the operating system, the object handle for establishing the wireless connection to the peripheral device, and
wherein issuing, by the application and using the object handle, the request to the operating system to establish the wireless connection to the peripheral device comprises issuing, by the application, to the API, and using the object handle, a request that the operating system establish the wireless connection to the peripheral device.

5. The method of claim 1, further comprising controlling, by the application and over the established wireless connection, one or more operations of the peripheral device.

6. The method of claim 1, wherein the object handle comprises unique identifying information for the peripheral device.

7. The method of claim 6, wherein the unique identifying information for the peripheral device comprises a media access control (MAC) address of the peripheral device.

8. The method of claim 6, wherein the unique identifying information for the peripheral device comprises at least one of a lot number, a device identifier, a software version, or a model of the peripheral device.

9. The method of claim 6,
further comprising issuing, by the application and to an Application Program Interface (API) for the operating system, a request to discover the peripheral device,
wherein receiving the object handle for establishing the wireless connection to the peripheral device comprises receiving, in response to the request to discover the peripheral device, the object handle for establishing the wireless connection to the peripheral device, and wherein determining the advertisement cadence for the peripheral device comprises determining, based on the unique identifying information for the peripheral device, the advertisement cadence.

10. The method of claim 9, wherein a clock of the application and a clock of peripheral device are asynchronous.

11. The method of claim 1, wherein determining the advertisement cadence for the peripheral device comprises determining, based on a correlation between a clock of the application and a clock of the peripheral device, the advertisement cadence.

12. The method of claim 11,
wherein the object handle comprises unique identifying information for the peripheral device, and
wherein determining, based on the correlation between the clock of the application and the clock of the peripheral device, the advertisement cadence comprises determining, based on the correlation between the clock of the application, the clock of the peripheral device, and the unique identifying information for the peripheral device, the advertisement cadence.

13. The method of claim 11, wherein the clock of the application and the clock of the peripheral device are synchronous.

14. The method of claim 1, wherein determining the amount of time required by the operating system to establish the wireless connection with the peripheral device comprises retrieving, from a look-up table for the application, the amount of time required by the operating system to establish the wireless connection with the peripheral device.

15. The method of claim 1, wherein the wireless connection is a Bluetooth® wireless connection.

16. The method of claim 1, wherein the operation system is at least one of an Android™ operating system or an iOS™ operating system.

17. The method of claim 1, wherein the peripheral device is an implantable medical device (IMD).

18. A device comprising:
a memory configured to store an operating system and an application for execution on the operating system; and
processing circuitry configured to execute the operating system and the application, wherein the application is configured to:
receive an object handle for establishing a wireless connection to a peripheral device of a plurality of peripheral devices, wherein the operating system creates the object handle to identify the peripheral device from other peripheral devices of the plurality of peripheral devices;
determine, based on the object handle, an advertisement cadence for the peripheral device, wherein the advertisement cadence comprises periods of time wherein the peripheral device is discoverable interleaved with periods of time wherein the peripheral device is non-discoverable; and
at a time determined based on the advertisement cadence, issue, using the object handle, a request to the operating system to establish the wireless connection to the peripheral device, such that the operating system establishes the wireless connection to the peripheral device during one of the periods of time wherein the peripheral device is discoverable.

19. The device of claim 18, wherein the application is further configured to determine an amount of time required by the operating system to establish the wireless connection to the peripheral device, and wherein, to issue the request to the operating system to establish the wireless connection to the peripheral device, the application is configured to issue the request to the operating system to establish the wireless connection to the peripheral device at a time determined based on the advertisement cadence and the amount of time required by the operating system to establish the wireless connection to the peripheral device, such that the operating system establishes the wireless connection to the peripheral device during one of the periods of time wherein the peripheral device is discoverable.

20. The device of claim 19, wherein, to determine the amount of time required by the operating system to establish the wireless connection to the peripheral device, the application is configured to determine the amount of time required by the operating system to establish the wireless connection to the peripheral device based on at least one of:
a version of the operating system;
a configuration of the processing circuitry; or
a model of the external computing device.

21. The device of claim 18,
wherein, to receive the object handle for establishing the wireless connection to the peripheral device, the application is configured to receive, from an Application Program Interface (API) for the operating system, the object handle for establishing the wireless connection to the peripheral device, and
wherein, to issue, using the object handle, the request to the operating system to establish the wireless connection to the peripheral device, the application is configured to issue, to the API and using the object handle, a request that the operating system establish the wireless connection to the peripheral device.

22. The device of claim 18, wherein the application is further configured to control, over the established wireless connection, one or more operations of the peripheral device.

23. The device of claim 18, wherein the object handle comprises unique identifying information for the peripheral device.

24. The device of claim 23, wherein the unique identifying information for the peripheral device comprises a media access control (MAC) address of the peripheral device.

25. The device of claim 23, wherein the unique identifying information for the peripheral device comprises at least one of a lot number, a device identifier, a software version, or a model of the peripheral device.

26. The device of claim 23, wherein the application is further configured to issue, to an Application Program Interface (API) for the operating system, a request to discover the peripheral device,
wherein, to receive the object handle for establishing the wireless connection to the peripheral device, the application is configured to receive, in response to the request to discover the peripheral device, the object handle for establishing the wireless connection to the peripheral device, and
wherein, to determine the advertisement cadence for the peripheral device, the application is further configured to determine, based on the unique identifying information for the peripheral device, the advertisement cadence.

27. The device of claim 26, wherein a clock of the application and a clock of peripheral device are asynchronous.

28. The device of claim 18, wherein, to determine the advertisement cadence for the peripheral device, the application is configured to determine, based on a correlation between a clock of the application and a clock of the peripheral device, the advertisement cadence.

29. The device of claim 28,
wherein the object handle comprises unique identifying information for the peripheral device, and
wherein to determine, based on the correlation between the clock of the application and the clock of the peripheral device, the advertisement cadence, the advertisement is configured to determine, based on the correlation between the clock of the application, the clock of the peripheral device, and the unique identifying information for the peripheral device, the advertisement cadence.

30. The device of claim 28, wherein the clock of the application and the clock of the peripheral device are synchronous.

31. The device of claim 18, wherein, to determine the amount of time required by the operating system to establish the wireless connection with the peripheral device, the application is configured to retrieve, from a look-up table for the application, the amount of time required by the operating system to establish the wireless connection with the peripheral device.

32. The device of claim 18, wherein the wireless connection is a Bluetooth® wireless connection.

33. The device of claim 18, wherein the operation system is at least one of an Android™ operating system or an iOS™ operating system.

34. A system comprising:
a peripheral device comprising communication circuitry, wherein the peripheral device further comprises an advertisement cadence, and wherein the advertisement cadence comprises periods of time wherein the peripheral device is discoverable interleaved with periods of time wherein the peripheral device is non-discoverable; and
an external computing device comprising:
a memory configured to store an operating system and an application for execution on the operating system; and
processing circuitry configured to execute the operating system and the application, such that the application is configured to:
receive an object handle for establishing a wireless connection to a peripheral device of a plurality of peripheral devices, wherein the operating system creates the object handle to identify the peripheral device from other peripheral devices of the plurality of peripheral devices;
determine, based on the object handle, the advertisement cadence for the peripheral device; and
at a time determined based on the advertisement cadence, issue, using the object handle, a request to the operating system to establish the wireless connection to the peripheral device, such that the operating system establishes the wireless connection to the peripheral device during one of the periods of time wherein the peripheral device is discoverable.

35. A non-transitory, computer-readable medium comprising instructions that, when executed, cause processing circuitry of an external computing device to execute an operating system and an application, such that the application is configured to:
receive an object handle for establishing a wireless connection to a peripheral device of a plurality of peripheral devices, wherein the operating system creates the object handle to identify the peripheral device from other peripheral devices of the plurality of peripheral devices;

determine, based on the object handle, an advertisement cadence for the peripheral device, wherein the advertisement cadence comprises periods of time wherein the peripheral device is discoverable interleaved with periods of time wherein the peripheral device is non-discoverable; and at a time determined based on the advertisement cadence, issue, using the object handle, a request to the operating system to establish the wireless connection to the peripheral device, such that the operating system establishes the wireless connection to the peripheral device during one of the periods of time wherein the peripheral device is discoverable.

* * * * *